(12) United States Patent
Ergler et al.

(10) Patent No.: US 10,765,389 B2
(45) Date of Patent: Sep. 8, 2020

(54) DETECTOR DEVICE COMPRISING A COOLING AIR PATHWAY FOR COOLING AN X-RAY DETECTOR

(71) Applicant: Siemens Healthcare GmbH, Erlangen (DE)

(72) Inventors: Thorsten Ergler, Erlangen (DE); Jan Wrege, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 141 days.

(21) Appl. No.: 15/985,871

(22) Filed: May 22, 2018

(65) Prior Publication Data

US 2018/0338736 A1 Nov. 29, 2018

(30) Foreign Application Priority Data

May 29, 2017 (DE) .......................... 10 2017 208955

(51) Int. Cl.
*A61B 6/00* (2006.01)
*A61B 6/03* (2006.01)

(52) U.S. Cl.
CPC .......... *A61B 6/4488* (2013.01); *A61B 6/4208* (2013.01); *A61B 6/035* (2013.01); *A61B 2560/0406* (2013.01)

(58) Field of Classification Search
CPC ............ A61B 2560/0406; A61B 6/035; A61B 6/4208; A61B 6/4488
See application file for complete search history.

(56) References Cited

U.S. PATENT DOCUMENTS

| 4,456,826 A | * | 6/1984 | Forster | .................. | A61B 6/035 |
| | | | | | 250/370.09 |
| 5,761,269 A | * | 6/1998 | Sugihara | ................ | A61B 6/035 |
| | | | | | 378/199 |
| 7,372,938 B2 | | 5/2008 | Pohan | | |

(Continued)

FOREIGN PATENT DOCUMENTS

| DE | 102004055752 A1 | 6/2006 |
| DE | 102006024972 A1 | 12/2007 |

(Continued)

OTHER PUBLICATIONS

Linke-Diesinger, Andreas: "Systeme von Turbofan-Triebwerken —Funktionen der Triebwerkssysteme von Verkehrsflugzeugen"; Chapter 2.2.3.3.; pp. 45-48; Springer Verlag; 2014; ISBN 978-3-662-44570-9.

(Continued)

*Primary Examiner* — Marcus H Taningco
(74) *Attorney, Agent, or Firm* — Harness, Dickey & Pierce, P.L.C.

(57) ABSTRACT

A detector device includes a cooling air pathway for cooling an X-ray detector. The detector device furthermore includes a detector interior space surrounding the X-ray detector. The cooling air pathway runs through at least one subregion of the detector interior space. The detector device includes a pressure limitation unit with a limitation device arranged along the cooling air pathway. The limitation device is designed, based on an incoming cooling air flow, to route a limited volume flow along the cooling air pathway at the X-ray detector.

23 Claims, 7 Drawing Sheets

(56) References Cited

U.S. PATENT DOCUMENTS

| | | | |
|---|---|---|---|
| 2005/0287008 A1* | 12/2005 | Lacey | A61B 6/4488 417/32 |
| 2006/0126782 A1 | 6/2006 | Pohan | |
| 2007/0284535 A1 | 12/2007 | Heismann | |
| 2010/0098210 A1 | 4/2010 | Hackenschmied | |
| 2015/0265232 A1* | 9/2015 | Kodaira | A61B 6/035 378/15 |
| 2015/0272525 A1 | 10/2015 | Kuhn | |
| 2016/0235378 A1* | 8/2016 | Yun | A61B 6/4488 |
| 2017/0105692 A1* | 4/2017 | Sawanobori | A61B 6/4488 |
| 2018/0059270 A1* | 3/2018 | Hefetz | G01T 1/244 |

FOREIGN PATENT DOCUMENTS

| | | |
|---|---|---|
| DE | 102008051045 A1 | 4/2010 |
| DE | 102013226666 A1 | 6/2015 |
| DE | 102014201741 A1 | 8/2015 |
| DE | 102014205739 A1 | 10/2015 |

OTHER PUBLICATIONS

Mahrla, Martin: „Der Strömungswiderstand mit einer Betrachtung des Strömungsverhaltens von Liegerädern; http://www.philippi-trust.de/hendrik/braunschweig/wirbeldoku/mahrla.html.
German Office Action #102017208955.5 dated Feb. 19, 2018.

* cited by examiner

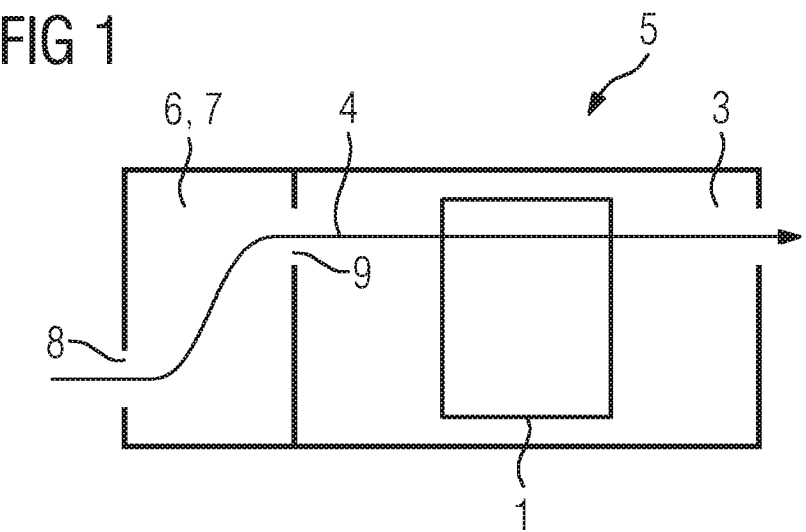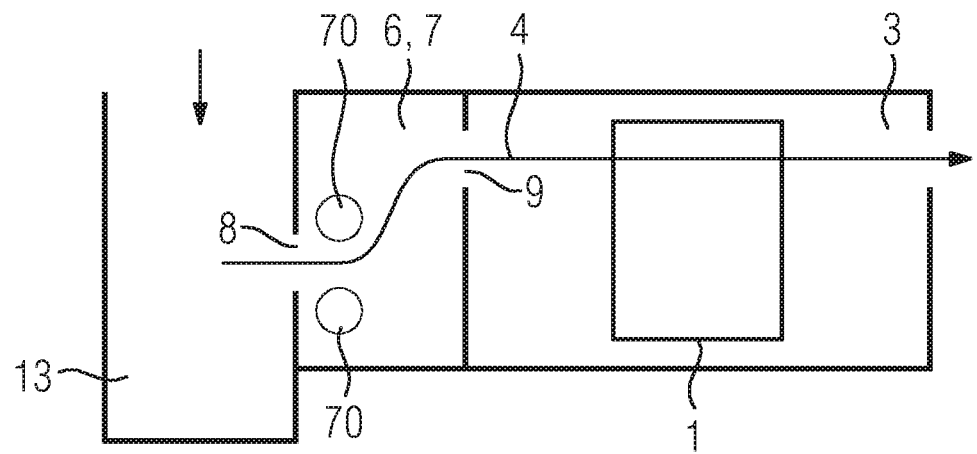

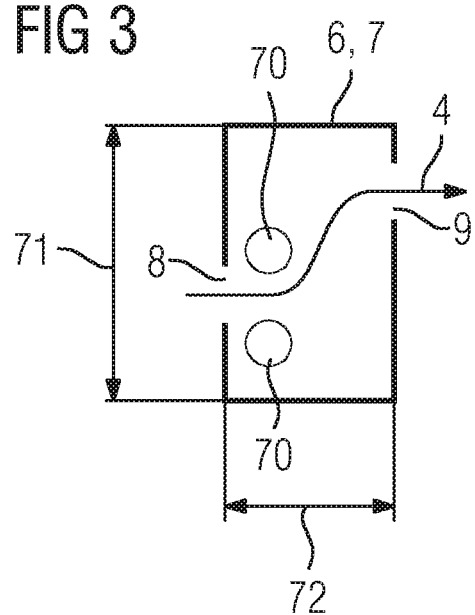
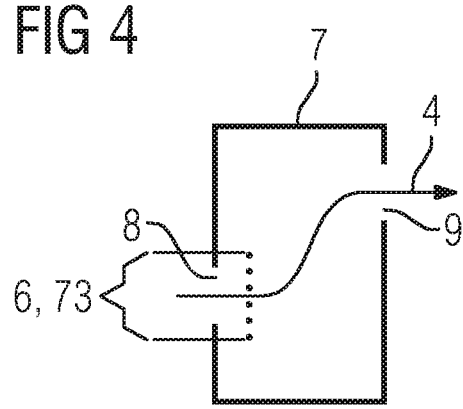
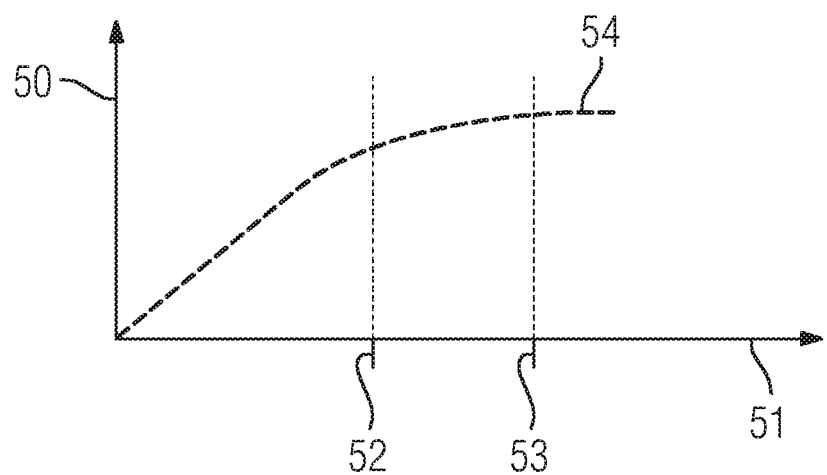

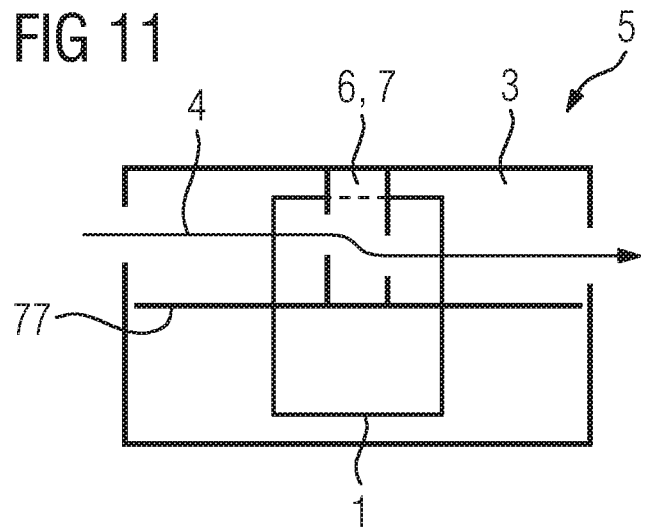
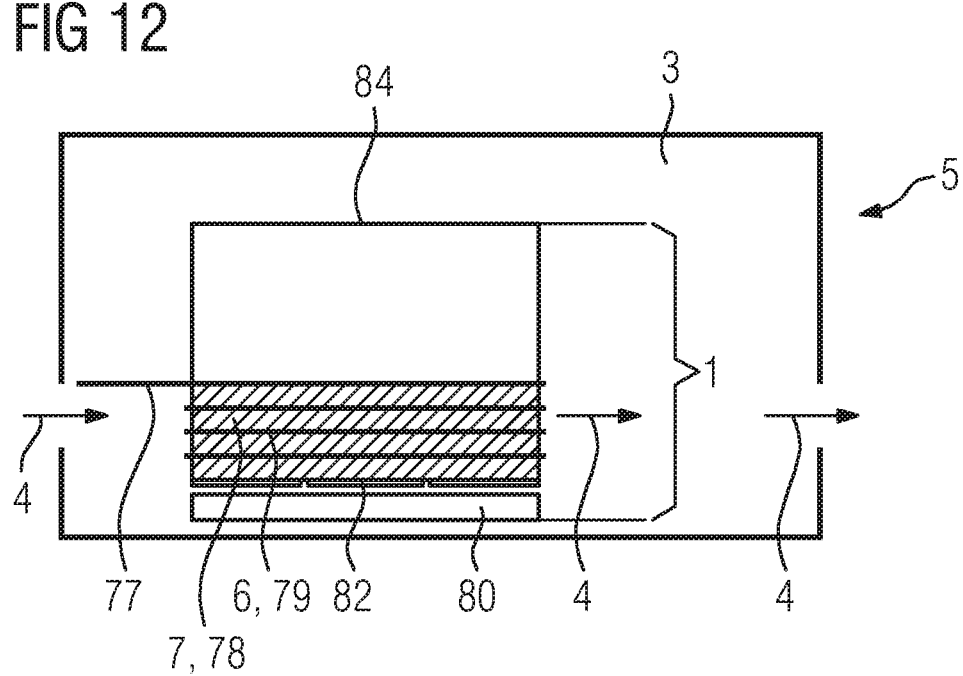

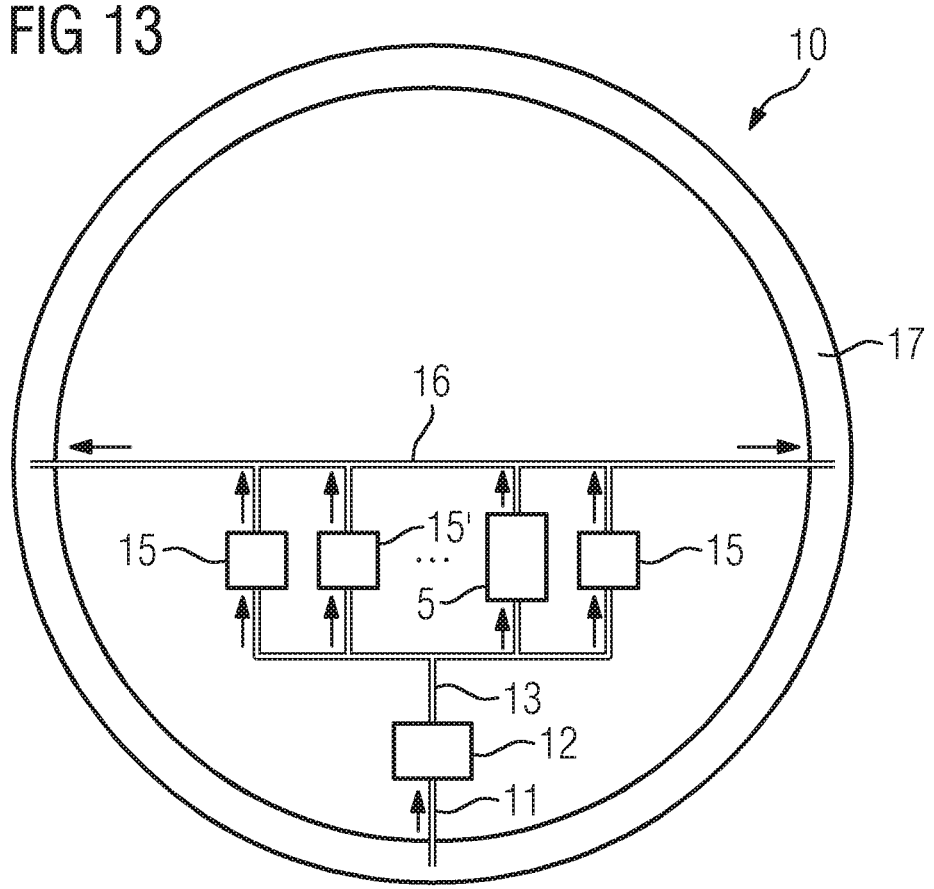

DETECTOR DEVICE COMPRISING A COOLING AIR PATHWAY FOR COOLING AN X-RAY DETECTOR

PRIORITY STATEMENT

The present application hereby claims priority under 35 U.S.C. § 119 to German patent application number DE 102017208955.5 filed May 29, 2017, the entire contents of which are hereby incorporated herein by reference.

FIELD

At least one embodiment of the invention generally relates to a detector device comprising a cooling air pathway for cooling an X-ray detector and/or a medical device for this purpose.

BACKGROUND

In X-ray imaging, for example in computed tomography, angiography or radiography, use can be made of counting direct conversion X-ray detectors or integrating indirect conversion X-ray detectors.

X-rays or photons in indirect conversion X-ray detectors can be converted into light by a suitable converter material and via photodiodes into electrical pulses. Scintillators, for example GOS (Gd2O2S), CsI, YGO or LuTAG, are frequently used as converter material. In particular, scintillators are used in medical X-ray imaging in the energy range up to 1 MeV. Customarily, so-called indirect conversion X-ray detectors, so-called scintillator detectors, are used, in which X-rays or gamma rays are converted into electrical signals in two stages. In a first stage, the X-ray or gamma quanta are absorbed in a scintillator element and converted into optically visible light; this effect is called luminescence. In a second stage, the light excited by luminescence is then converted into an electrical signal by a first photodiode optically coupled to the scintillator element, read out by way of evaluation or read-out electronics and subsequently forwarded to a computing unit.

The X-rays or the photons in direct conversion X-ray detectors can be converted into electrical pulses by a suitable converter material. For example CdTe, CZT, CdZnTeSe, CdTeSe, CdMnTe, InP, TlBr$_2$, HgI$_2$, GaAs or others can be used as converter material, in particular for use in a computed tomography system. The electrical pulses are evaluated by evaluation electronics, for example an integrated circuit (Application Specific Integrated Circuit, ASIC). In counting X-ray detectors, incident X-rays are measured by counting the electrical pulses which are triggered by the absorption of X-ray photons in the converter material. As a rule, the level of the electrical pulse is proportionate to the energy of the absorbed X-ray photon. By comparing the level of the electrical pulse with a threshold value, spectral information can be extracted.

A detector unit of a computed tomography system is known from the publication DE 10 2004 055 752 A1. The detector unit comprises a footprint which faces a support ring of a gantry of the computed tomography system in an assembly position, and a detector surface which is angled approximately vertically away from the footprint and faces an isocentric axis of the gantry in the assembly position and along which a number of detector elements for the detection of X-rays are positioned. The footprint has an air inlet which is fitted in such a way that a cooling air flow externally impinging on the footprint is routed to the inside of the detector surface. In the assembly position, the air inlet corresponds to an air duct in the support ring or routed between the winding carriage and the support ring.

An X-ray detector module comprising a sensor layer with a sensor surface in a stack formation is known from the publication DE 10 2013 226 666 A1, wherein a high voltage can be applied to the sensor surface for the detection of X-rays, wherein the sensor layer is thermally coupled to a latent heat storage system.

It is known from the publication DE 10 2014 201 741 A1 that in order to adjust the temperature of an X-ray detector of an X-ray machine comprising a plurality of adjacently arranged detector elements in which the X-ray detector and/or an X-ray source are moved relative to a measurement object during the acquisition of an X-ray image, a respective heat input measurement from the detector elements characteristic of the heat input into this detector element is recorded during the acquisition of the X-ray image, and the respective heat input measurement recorded for each detector element is taken into account when adjusting the temperature of at least one other detector element.

A radiation direct converter designed for the detection of X-rays and operated with a direct converter element having a temperature of at least 38° C. and at most 55° C. is known from the publication DE 10 2008 051 045 A1. The temperature can be adjusted via a Peltier element or an air flow.

In the operation of the medical device, the source of radiation and/or X-ray tube, in particular at high or full tube output, heats up greatly and must then be cooled down again as quickly as possible when treating patients to enable the recording of subsequent images. This is done by briefly increasing the fan speed of a cooling unit to the maximum value. This increases the pressure difference between the air intake side and the exhaust side and thus the amount of air which is transported through the so-called tube cooler. As the other users are connected to the tube cooler in parallel, however, these are now cooled in an above-average manner. As a rule, this does not disrupt the existing users as their work areas are designed for a particular, generally very generous temperature range and not for a temperature point. A direct conversion X-ray detector should display a constant operating temperature, however.

SUMMARY

In at least one embodiment of the invention, the resistance of the converter material can change with the X-ray flux. This also leads to a so-called HV current variation in the converter element and thus to a change in the power loss. A change in temperature can influence the counting rate and the energy resolution. The X-ray detector can thereby suffer from a temperature-dependent counting rate drift which can lead to artifacts in imaging. As the detected dose changes during a scan and/or a recording in computed tomography imaging, this may involve a time-dependent and/or a dynamic effect which should be compensated by appropriate temperature stabilization measures.

At least one embodiment of the invention is directed to a detector device and/or a medical device which enable a limitation of the maximum volume flow of the cooling air along the X-ray detector.

An embodiment of the invention is directed to a detector device. Another embodiment is directed to a medical device.

At least one embodiment of the invention relates to a detector device comprising a cooling air pathway for cooling an X-ray detector. Furthermore, the detector device has a detector interior space surrounding the X-ray detector, wherein the cooling air pathway runs through at least one subregion of the detector interior space. Furthermore, the detector device has a pressure limitation unit arranged along the cooling air pathway with a limitation device, wherein the limitation device is designed to route a limited volume flow along the cooling air pathway at the X-ray detector based on an incoming cooling air flow. The pressure limitation unit can be a pressure antechamber arranged upstream relative to the detector interior space. The pressure limitation unit can be a pressure after-chamber arranged downstream relative to the detector interior space. The pressure limitation unit can be a pressure intermediate chamber arranged in the detector interior space. The pressure limitation unit can be designed as a heat sink at the X-ray detector.

Furthermore, at least one embodiment of the invention relates to a medical device comprising a detector device according to at least one embodiment of the invention and a cooling circuit. The cooling circuit has a supply air duct from an air duct to a cooling unit, at least one cooling air duct from the cooling unit to the detector device, and an exhaust air duct from the detector device to the air duct.

According to an embodiment of the invention, the medical device is a computed tomography system. The rotor may comprise the detector device and the cooling circuit. Advantageously, the cooling can be fully realized inside the rotor.

BRIEF DESCRIPTION OF THE DRAWINGS

Example embodiments of the invention are explained in more detail below with reference to the diagrams. The diagrams show:

FIG. 1 A diagrammatic view of a detector device according to the invention in a first embodiment;

FIG. 2 A diagrammatic view of a detector device according to the invention in a second embodiment;

FIG. 3 A diagrammatic view of a pressure limitation unit according to the invention in a first embodiment;

FIG. 4 A diagrammatic view of a pressure limitation unit according to the invention in a second embodiment;

FIG. 5 A diagrammatic view of a first characteristic of the limited volume flow as a function of the pressure;

FIG. 11 A diagrammatic view of a detector device according to the invention in a sixth embodiment;

FIG. 12 A diagrammatic view of a detector device according to the invention in a seventh embodiment;

FIG. 13 A diagrammatic view of a cooling circuit according to an embodiment of the invention.

DETAILED DESCRIPTION OF THE EXAMPLE EMBODIMENTS

Figure 6:
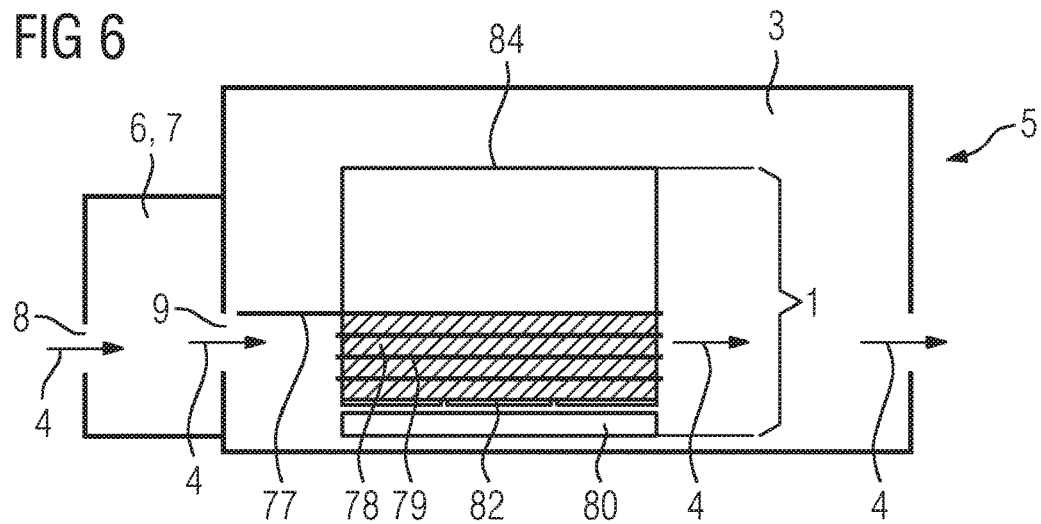
FIG. 6 A diagrammatic view of a detector device according to the invention in a third embodiment.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a detector device comprising a cooling air pathway for cooling an X-ray detector. Furthermore, the detector device has a detector interior space surrounding the X-ray detector, wherein the cooling air pathway runs through at least one subregion of the detector interior space. Furthermore, the detector device has a pressure limitation unit arranged along the cooling air pathway with a limitation device, wherein the limitation device is designed to route a limited volume flow along the cooling air pathway at the X-ray detector based on an incoming cooling air flow. The pressure limitation unit can be a pressure antechamber arranged upstream relative to the detector interior space. The pressure limitation unit can be a pressure after-chamber arranged downstream relative to the detector interior space. The pressure limitation unit can be a pressure intermediate chamber arranged in the detector interior space. The pressure limitation unit can be designed as a heat sink at the X-ray detector.

In an embodiment, the detector device can have an indirect conversion or/and direct conversion X-ray detector. The detector direction can preferably have a direct conversion X-ray detector. The X-ray detector is embodied in the detector interior space. The detector interior space can, in particular, have an inlet opening and an outlet opening for cooling air. The detector interior space can essentially be designed in such a gas-tight manner that the cooling air can only be routed into the detector interior space and/or routed out of the detector interior space through the inlet opening and the outlet opening respectively.

Cooling air flows through the detector device along a cooling air pathway during operation. In an embodiment, the cooling air pathway passes through at least one subregion of the detector interior space. The detector device has a pressure limitation unit. The pressure limitation unit can be arranged in the detector interior space along the cooling air pathway or relative to the detector interior space upstream or downstream along the cooling air pathway. The pressure limitation unit can be connected to the inlet opening of the detector interior space such that the cooling air can flow from the pressure limitation unit into at least one subregion of the detector interior space.

A cooling air flow flows into the pressure limitation unit during operation. In an embodiment, the pressure limitation unit has a limitation device which can reduce the pressure of the cooling air flow flowing into at least the subregion of the detector interior space and/or the volume flow via the pressure limitation unit. The cooling air pathway runs through the pressure limitation unit and/or in the case of the heat sink as a pressure limitation unit along the pressure limitation unit. The pressure limitation unit can have an inlet opening and an outlet opening. The outlet opening of the pressure limitation unit can be mechanically, preferably directly, connected to the inlet opening of the detector interior space, wherein the limited volume flow is routed into the detector interior space preferably precisely. The cooling air pathway may comprise a cooling circuit. The cooling air pathway can, in particular, pass through the pressure limitation unit and the detector interior space. The cooling circuit essentially has no gas exchange with volume outside the cooling circuit.

In an embodiment, the cooling air flow of the cooling air duct of the cooling circuit can be at least partially conducted into a pressure limitation unit; particularly at high pressures the volume flow through the detector interior space can be reduced via the limitation unit to avoid excessive cooling of the X-ray detector.

In an embodiment, the X-ray detector can have a heating unit, in particular with a heating control. The heating unit can, in particular, heat the converter element. The heating unit can stabilize the temperature of the converter element.

The inventors have recognized that the power loss in the converter element can be proportional to the X-ray flux. During a clinical scan the X-ray flux may vary, possibly causing a fluctuating power loss of the converter element. This power loss fluctuation can be translated into a temperature fluctuation of the converter element.

Any heating control can be based on these power loss fluctuations being compensated by a correspondingly inversely operated heating unit such that overall constant power is always consumed in the converter element and the temperature is kept stable.

In an embodiment, the converter element can be heated to a constant level. If X-rays are incident and this creates an additional loss of power, the heat output may be reduced accordingly. The heating control can be designed such that the temperature in the converter element is kept constant in a narrow temperature window, for example +/−5 K, preferably +/−1 K. The observance of boundary conditions may be necessary for temperature stabilization.

In an embodiment, the maximum heat output which is introduced into the converter element without the influence of X-rays can as a first boundary condition be so high that it can compensate the maximum relevant X-ray flux during clinical operation or during calibration operation. A briefly higher X-ray flux can be compensated by the thermal mass of the detector device and/or the X-ray detector.

As a second boundary condition the maximum heat output can be so high that at the maximum cooling capacity of the system cooling, for example triggered by a cooling process of the X-ray tube, the X-ray detector can maintain its operating temperature and is not undercooled. The problem of undercooling of the X-ray detector and/or the converter element can be achieved by a pressure limitation unit before the inlet opening of the detector interior space, after the outlet opening of the detector interior space or in the detector interior space. As the volume flow increases, the amount of turbulence in the pressure limitation unit may increase and result in less air being transported through the pressure limitation unit and/or through the detector interior space and/or along the X-ray detector.

Instead of adjusting the maximum heat output to the maximum cooling capacity of the cooling circuit, the volume flow can be limited according to the invention so that the maximum cooling capacity cannot result in excessive cooling of the X-ray detector. Vortex formation in the pressure limitation unit can be influenced via the limitation device. Vortex formation can increase as a function of the Reynolds number. The limitation device can be designed such that as of a predetermined pressure and/or as of a predetermined flow velocity an increasing and/or intensified vortex formation limits the volume flow. The additional noise generated by the vortex formation can be reduced by insulation, in particular noise insulation, of the pressure limitation unit or the detector device. The additional noise generation as a result of vortex formation may be advantageously lower than the volume of the cooling unit and/or the fan.

Advantageously, undercooling and/or excessive cooling of the X-ray detector and/or the converter element can be avoided. Advantageously, the dynamic heating range of the temperature control can be kept in a currently technically feasible range. Advantageously, the costs for the detector can be reduced. Advantageously, the service life of the X-ray detector and/or the detector unit can be extended as the yielded heat output of the heating unit can be designed to be lower. Advantageously, the dynamic heating range of the temperature control can be kept in a currently technically feasible range. Advantageously, the service life of the detector device increases if the yielded heat output is designed to be lower. The air resistance in the detector interior space can be advantageously minimized so that the conducted amount of air is increased. Advantageously, noise generation can be kept low so that the fan or ventilator for transporting the cooled air to the detector device can be in a range of 500 to 800 revolutions per minute.

According to an embodiment of the invention, the pressure limitation unit is arranged downstream relative to the detector interior space. The pressure limitation unit can be designed as a pressure after-chamber. According to an embodiment of the invention, the pressure limitation unit is arranged in the detector interior space. The pressure limitation unit can be designed as a pressure intermediate chamber or as a heat sink. According to an embodiment of the invention, the heat sink comprises the pressure limitation unit. The pressure limitation unit can be designed as a pressure antechamber. Advantageously, the volume flow along the cooling air pathway can be limited such that the cooling of the X-ray detector is limited.

According to an embodiment of the invention, the pressure limitation unit is arranged upstream relative to the detector interior space. Based on the cooling air flowing into the pressure limitation unit, the limitation device can be designed to guide the limited volume flow from the pressure limitation unit along the cooling air pathway into the detector interior space. Furthermore, the detector device may have a pressure limitation unit with a limitation device arranged upstream relative to the detector interior space along the cooling air pathway, wherein the limitation device is designed to guide a limited volume flow from the pressure limitation unit along the cooling air pathway into the detector interior space based on cooling air flowing into the pressure limitation unit.

According to an embodiment of the invention, one of a height, a width, a depth, an inlet opening or/and an outlet opening of the limitation device, in particular a pressure antechamber, a pressure intermediate chamber or a pressure after-chamber, is designed to limit a volume flow based on an incoming cooling air flow. Through appropriate selection of the height, width and/or depth, the vortex formation in the pressure limitation unit can be influenced. Through appropriate selection of the position and/or size of the inlet opening or/and the outlet opening of the pressure limitation unit, the vortex formation in the pressure limitation unit can be influenced. Advantageously, the limitation unit can be selected such that the volume flow in the detector interior space is limited. The limitation unit can correspond to the embodiment of the pressure limitation unit and/or the pressure limitation unit.

According to an embodiment of the invention, the detector device has an air guide element which is designed to guide along the limited volume flow at a subregion of the X-ray detector, in particular at the converter element or the heat sink. The air guide element can divide the detector interior space into at least two zones, wherein one zone comprises the subregion of the X-ray detector. The two zones can be separated from one another in such a way that the limited volume flow can only flow through the zone comprising the subregion of the X-ray detector along the cooling air pathway. The subregion of the X-ray detector preferably comprises the converter element. Advantageously, the limited volume flow can cool the X-ray detector and/or the converter element. Advantageously, the subregion of the X-ray detector can be protected from further temperature influences, for example further cooling air in the other zone.

According to an embodiment of the invention, the limitation device, in particular of a pressure antechamber, comprises a valve. Advantageously, the valve can be opened above a predetermined pressure. Advantageously, the valve is designed to limit the volume flow.

The valve can be designed between the pressure limitation unit and the detector interior space. In particular, the valve can be a bleed valve. The valve can be embodied between the pressure channel and/or cooling air duct and detector interior space. The valve can open at a predetermined pressure and/or volume flow, in particular at a volume flow which is too high for the X-ray detector. Part of the volume flow can be guided in particular into the other zone of the detector interior space separated by the air guide element so that the subregion of the X-ray detector itself is not cooled by this part of the volume flow. Alternatively, the valve can also blow the part of the volume flow into the surroundings past the detector interior. By opening the valve, air can be guided into the detector interior space, whereby the pressure in the detector interior space can be increased therein and the differential pressure along the heat sink thus reduced. The volume flow can be reduced as a result. The opening and/or the switching point of the valve can be designed such that at the maximum fan speed of the cooling unit in the gantry and/or in the rotor, the volume flow along the X-ray detector and/or the subregion of the X-ray detector, in particular any cooling fins of a heat sink, does not exceed a maximum value and/or that the undercooling of the X-ray detector is prevented. Advantageously, the volume flow can be limited and an undercooling of the X-ray detector avoided.

The valve can be controlled purely mechanically, for example analogously to bleed valves in engine technology. In particular, mechanical control may comprise spring mechanisms, bimetals, etc. Advantageously, the valve can be reliably and favorably controlled. The valve can be switched and/or controlled via an active controller, for example via magnetic switches, piezoelectric switches, a motor, etc. Advantageously, the valve can be variably controlled.

According to an embodiment of the invention, the valve has a switching point for automatic opening of the valve. The switching point itself can be defined by one or various parameters or/and a measured value or various measured values. A parameter or a measured value can be a pressure in the antechamber, a temperature at the sensor board, or a fan speed of the cooling unit. A temperature sensor can be provided in the cooling air flow or on other components, a volume flow meter or the like in the detector device or the cooling circuit. Advantageously, the volume flow can be automatically and reliably limited. The switching point can denote a predetermined, in particular, maximum, pressure in the pressure limitation unit.

According to an embodiment of the invention, a partial flow rate guided through the valve is protected from the subregion of the X-ray detector via the air guide element. Advantageously, the partial flow rate cannot cool the subregion of the X-ray detector. Advantageously, the volume flow for cooling the subregion of the X-ray detector, in particular the converter element, can be limited.

According to an embodiment of the invention, the limitation device comprises one or more turbulence-producing bodies. The turbulence-producing body can limit the volume flow advantageously. The turbulence-producing body may be characterized by a Reynolds number. The Reynolds number of the turbulence-producing body can be selected such that in particular, as of a predetermined pressure or predetermined volume flow, the turbulence occurs more frequently.

Advantageously, the volume flow can be limited, in particular as of a predetermined pressure. The turbulence-producing body can be a rod, for example with a round, square or drop-shaped cross-section. The turbulence-producing body and/or the limitation device can for example be designed as cooling fins on the heat sink. The cooling fins can be designed such that the volume flow is limited by an increased vortex formation.

According to an embodiment of the invention, the turbulence-producing body is a grid. The grid may comprise a multiplicity of lattice rods. The lattice rods may have suitable identical or different cross-sections. The lattice rods may be arranged at constant or variable angles or densities in one plane or in a plurality of planes, for example perpendicular to the cooling air pathway.

Advantageously, the dependence of the volume flow on the pressure can be predetermined via the embodiment of the grid.

According to an embodiment of the invention, the detector device has a heat sink connected to the X-ray detector in a thermally conductive manner around which the limited volume flow can flow. The pressure limitation unit can be designed as a heat sink. The heat sink may comprise the subregion of the X-ray detector. The heat sink may have cooling fins or other cooling structures. The heat sink can be cooled by the limited volume flow. The X-ray detector can be cooled via the heat sink. Advantageously, the heat sink can ensure a uniform operating temperature of the X-ray detector and/or the converter element. The heat sink can advantageously reduce brief temperature fluctuations of the X-ray detector.

According to an embodiment of the invention, the operating temperature of the X-ray detector is constant. The operating temperature can be accurately set to +/−5 K. Preferably, the operating temperature can be kept constant at exactly 1 K. Advantageously, a stable range and/or a stable counting rate of the X-ray detector can be achieved.

According to an embodiment of the invention, the X-ray detector has a direct conversion converter element. The direct conversion converter material may preferably comprise CdTe or CZT. The power loss from direct conversion X-ray detectors compared to indirect conversion X-ray detectors may be significantly greater, wherein the greater power loss can be dissipated by an increased cooling air flow. To achieve this, the amount of air can be increased by the detector interior space. On the one hand, this can be achieved by increasing the pressure difference between the inlet opening and the outlet opening of the detector interior space and/or the pressure limitation unit, for example by increasing the fan speed. Advantageously, a stable counting rate of the direct conversion X-ray detector can be achieved.

Furthermore, at least one embodiment of the invention relates to a medical device comprising a detector device according to at least one embodiment of the invention and a cooling circuit. The cooling circuit has a supply air duct from an air duct to a cooling unit, at least one cooling air duct from the cooling unit to the detector device, and an exhaust air duct from the detector device to the air duct.

In a cooling unit, the air drawn in by a fan can be cooled. The cooled air can be transported in an interior space of the gantry and/or in a cooling air duct of the rotor to the detector interior space. The cooled air can be routed through the detector interior space for cooling. After the detector interior space, the air which has now been warmed is routed by way of an exhaust air duct and an air duct back to the cooling unit, cooled there and again supplied to the X-ray detector. Alternatively, the cooled air can be drawn in from the surroundings of the service room of the hospital or the practice. In the design of the cooling of the entire computed tomography system, low noise generation can be advantageous. The noise generation induced by the cooling air may advantageously not exceed a certain value in order not to impair the treatment of patients.

According to an embodiment of the invention, the medical device is a computed tomography system. The rotor may comprise the detector device and the cooling circuit. Advantageously, the cooling can be fully realized inside the rotor.

According to an embodiment of the invention, the air duct comprises a rotor and/or a gantry. Advantageously, the air duct can be designed along the rotor to enable the distribution of the cooling air to the detector device and further components.

According to an embodiment of the invention, at least one further cooling air duct is connected to one component, in particular further components. The further cooling air duct can be connected and/or designed in the cooling circuit parallel to the cooling air duct. The cooled air can be routed from the cooling unit by way of the further cooling air duct to the component. Advantageously, further components can be cooled parallel to the detector device and in conjunction with the same cooling circuit. After the detector interior space and any components, the air which has now been warmed is routed by way of an exhaust air duct and an air duct back to the cooling unit, cooled there and again supplied to the X-ray detector and any further components. Advantageously, the further components can be cooled via a volume flow different from the limited volume flow. Advantageously, the limitation device can limit the cooling capacity for the X-ray detector.

FIG. 1 shows an example embodiment of the detector device 5 according to the invention in a first embodiment. The detector device 5 has a cooling air pathway 4 for cooling an X-ray detector 1. Furthermore, the detector device 5 has a detector interior space 3 surrounding the X-ray detector 1, wherein the cooling air pathway 4 runs through at least one subregion of the detector interior space 3. Furthermore, the detector device 5 has a pressure limitation unit 7 with a limitation device 6 arranged upstream relative to the detector interior space 3 along the cooling air pathway 4, wherein the limitation device 6 is designed, based on cooling air flowing into the pressure limitation unit 7, to route a limited volume flow from the pressure limitation unit 7 along the cooling air pathway 4 into the detector interior space 3. The pressure limitation unit 7 is a pressure antechamber. The pressure limitation unit 7 and the detector interior space 3 are connected to one another by way of the outlet opening 9 of the pressure limitation unit 7 such that the limited volume flow can essentially flow along the cooling air pathway 4 into the detector interior space 3. The cooling air pathway 4 runs from the inlet opening 8 of the pressure limitation unit 7 through the pressure limitation unit 7 and the detector interior space 3. The flow direction of the cooled air and/or of the limited volume flow essentially runs along the cooling air pathway 4. The X-ray detector 1 has a direct conversion converter element. The operating temperature of the X-ray detector 1, in particular of the converter element, is constant.

FIG. 2 shows an example embodiment of the detector device according to the invention in a second embodiment. The pressure limitation device 7 is a pressure antechamber. The detector device is connected to the cooling air duct 13 at the inlet opening 8 such that the cooled air flows at a pressure, defined for example by the cooling unit or a fan, from the cooling air duct 13 into the pressure limitation unit 7. The inlet openings 8 or/and the outlet openings 9 are preferably round or oval. The cooling air pathway 4 partially runs through the cooling air duct 13. The cooling air duct 13 can also be referred to as a pressure channel. Downstream behind the inlet opening 8 of the pressure limitation unit 7 turbulence 70 is generated. The turbulence 70 influences the flow velocity and/or the pressure of the cooled air.

FIG. 3 shows an example embodiment of a pressure limitation unit 7 according to the invention in a first embodiment. The pressure limitation device 7 is a pressure antechamber, a pressure intermediate chamber or a pressure after-chamber. The pressure limitation unit 7 has a height 71, a width 72 and a depth. The height 71, the width 72 and the depth can each run perpendicular or at another angle unequal to 0 degrees to each other. The limitation device 6 comprises a height 71 of the pressure limitation unit 7, a width 72 of the pressure limitation unit 7, a depth of the pressure limitation unit 7, an inlet opening 8 of the pressure limitation unit 7 and an outlet opening 9 of the pressure limitation unit 7. The limitation device 6 is embodied by the pressure limitation unit 7 and its embodiment. The volume flow is limited by an appropriate selection of the height 71, the width 72, the depth, the inlet opening 8 and the outlet opening 9. The shape and/or the cross-sectional surface of the opening of the inlet opening 8 and/or the outlet opening 9 can be adjusted. Thus the characteristic curve is adjusted for the volume flow as a function of the pressure.

FIG. 4 shows an example embodiment of a pressure limitation unit 7 according to the invention in a second embodiment. The pressure limitation device 7 is a pressure antechamber, a pressure intermediate chamber or a pressure after-chamber. The limitation device 6 comprises a turbulence-producing body 73. The turbulence-producing body 73 is a grid. The turbulence-producing body 73 generates velocity turbulence as of a certain flow velocity. The lattice rods of the grid may have different diameters or cross-section shapes. The turbulence-producing body 73 is arranged in the pressure limitation unit 7 close to the inlet opening 8 on the cooling air pathway 4.

FIG. 5 shows an example embodiment of a first characteristic 54 of the limited volume flow 50 as a function of the pressure 51 for a pressure limitation unit of the first embodiment or the second embodiment or the pressure limitation unit comprising the heat sink. The characteristic 54 of the limited volume flow 50 in the detector interior space and/or along at least the subregion of the X-ray detector is shown as a function of the pressure 51 in the cooling air duct. The limited volume flow 50 increases to a first pressure 52 essentially linearly with the pressure 50. Between the first pressure 52 and the second pressure 53, the slope of the characteristic 54 of the limited volume flow 50 decreases as a function of the pressure 51. As of the second pressure 53, the limited volume flow 50 is essentially constant with further increasing pressure 51. The limitation unit generates increased turbulence with increasing pressure 51 such that a limitation of the volume flow 50 is achieved in the detector interior space.

FIG. 6 shows an example embodiment of the detector device according to the invention 5 in a third embodiment. The pressure limitation unit 7 is a pressure antechamber. During operation, the X-ray detector 1 has a scattered radiation grid 80 in a stacked arrangement along the direction of beam incidence of the X-rays, a multiplicity of direct conversion converter elements 82 arranged side by side in a plane, a heat sink 78 with cooling fins 79 and module electronics 84. The heat sink 78, around which the limited volume flow can flow, is connected to the X-ray detector 1 in a thermally conductive manner. The cooling air pathway 4 runs along the heat sink 78. The cooling fins 79 can be arranged parallel to the cooling air pathway 4. Furthermore, the X-ray detector 1 has an air guide element 77 between the module electronics 84 and the heat sink 78 such that a subregion of the X-ray detector 1 is essentially separated by the air guide element 77. The air guide element 77 is designed to route the limited volume flow along a subregion of the X-ray detector 1. From the cooling air duct, the cooled air is routed into the pressure limitation unit 7. The pressure distribution of the cooled air is homogenized in the pressure limitation unit and routed into the detector interior space 3 as a limited volume flow. The air guide element 77 guides the limited volume flow along the cooling air pathway 4 to the cooling fins 79 and/or the heat sink 78 and/or the subregion of the X-ray detector 1. In this way, the converter elements 82 are cooled. The scattered radiation grid 80 is used to suppress scattered radiation.

Figure 7:
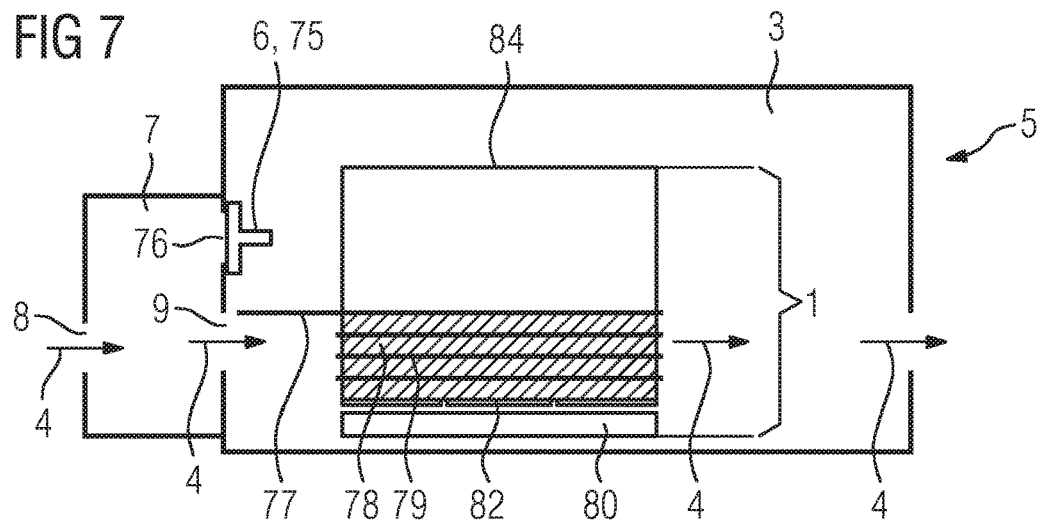
FIG. 7 A diagrammatic view of a detector device according to the invention in a fourth embodiment in a first state.

FIG. 7 shows an example embodiment of the detector device 5 according to the invention in a fourth embodiment in a first state. The pressure limitation unit 7 is a pressure antechamber. The limitation device 6 comprises a valve 75. The valve 75 is shown in a closed state such that a further outlet opening 76 is closed.

Figure 8:
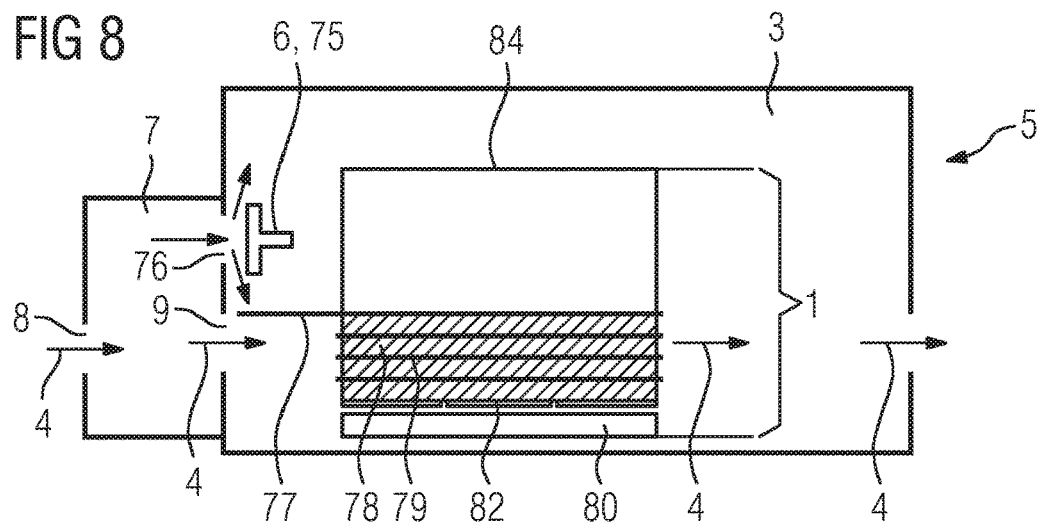
FIG. 8 A diagrammatic view of a detector device according to the invention in a fourth embodiment in a second state.

FIG. 8 shows an example embodiment of the detector device 5 according to the invention in a fourth embodiment in a second state. The pressure limitation unit 7 is a pressure antechamber. The valve 75 is shown in an open state such that the further outlet opening 76 is open. The valve 75 has a switching point to automatically open the valve 75. A partial flow rate routed through the valve 75 is shielded from the subregion of the X-ray detector 1 via the air guide element 77.

Figure 9:
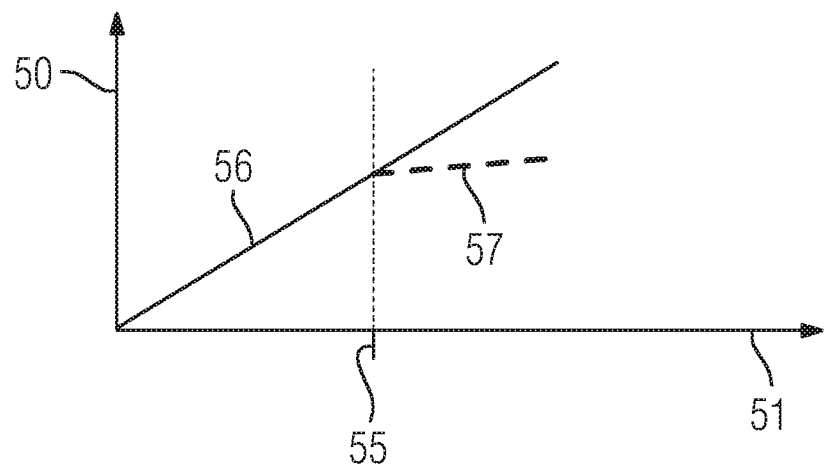
FIG. 9 A diagrammatic view of a second characteristic of the limited volume flow as a function of the pressure.

FIG. 9 shows an example embodiment of the second characteristic 56, 57 of the limited volume flow 50 as a function of the pressure 51 for a detector device according to the fourth embodiment. The limited volume flow 50 along the cooling fins is shown as a function of the pressure 51 in the closed state 56 and in the open state 57 of the valve. The limited volume flow 50 increases essentially linearly with the pressure 50 in the closed state 56 of the valve until a switching point 55. At the switching point 55 the valve opens. Above the switching point 55 and/or in the open state 57, the slope of the characteristic 54 of the limited volume flow 50 decreases as a function of the pressure 51. The limitation of the volume flow 50 in the detector interior space is achieved by opening the valve.

At the switching point 55 which for example can be defined by a pressure or a temperature at the converter element, the limited volume flow 50 along the cooling fins of the X-ray detector can be limited by opening the valve. The opening of the valve is designed such that at maximum fan speed, for example at the cooling unit, and/or maximum pressure 51 in the cooling air duct, the limited volume flow 50 along the cooling fins of the X-ray detector does not exceed a maximum value and/or that the undercooling of the X-ray detector is prevented.

Figure 10:
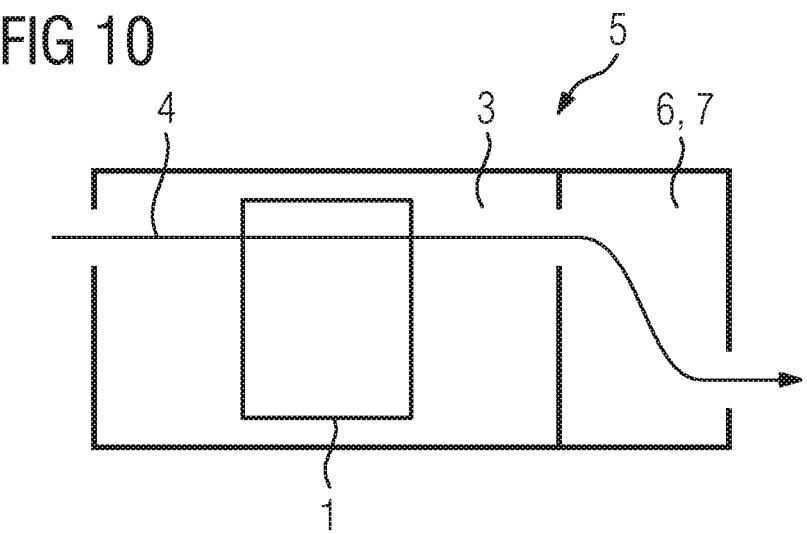
FIG. 10 A diagrammatic view of a detector device according to the invention in a fifth embodiment.

FIG. 10 shows an example embodiment of a detector device 5 according to the invention in a fifth embodiment. The pressure limitation unit 7 is a pressure after-chamber. The pressure limitation unit 7 is arranged downstream relative to the detector interior space 3. The pressure limitation unit 7 comprises a limitation device 6 of the first embodiment or the second embodiment. The cooling air pathway 4 runs through the detector interior space 3 and then through the pressure limitation unit 7.

FIG. 11 shows an example embodiment of a detector device 5 according to the invention in a sixth embodiment. The pressure limitation unit 7 is a pressure intermediate chamber. The pressure limitation unit 7 is embodied in the detector interior space 3. The pressure limitation unit 7 comprises a limitation device 6 of the first embodiment or the second embodiment. The pressure limitation unit 7 is embodied at the X-ray detector 1. The cooling air pathway 4 runs through the detector interior space 3, wherein the pressure limitation unit 7 is arranged in the detector interior space 3. The cooling air pathway 4 runs along at least the subregion of the X-ray detector 1.

FIG. 12 shows an example embodiment of a detector device 5 according to the invention in a seventh embodiment. The pressure limitation unit 7 is the heat sink 78. The limitation device 6 comprises at least one cooling fin 79. The cooling air pathway 4 runs through the detector interior space 3, wherein the pressure limitation unit 7, 78 is arranged in the detector interior space 3. The cooling fins 79 are designed such that the volume flow is limited.

FIG. 13 shows an example embodiment of a cooling circuit 10 according to the invention. The cooling circuit 10 has a supply air duct 11 from an air duct 17 to a cooling unit 12, at least one cooling air duct 13 from the cooling unit 12 to the detector device 5, and an exhaust air duct 16 from the detector device 5 to the air duct 17. At least one further cooling air duct 13 is connected to a component 15, 15'. The air duct 17 is comprised by the rotor of a computed tomography system. The cooling unit 12 may comprise a fan. The cooling unit 12 can be designed as an air or water cooler. The cooling unit 12 can draw and then cool air from the air duct 17, for example via a fan. A fan or ventilator transports the cooled air into the cooling air duct 13 to the detector device 5 and the components 15, 15'. The fan and/or ventilator can be operated at up to 3000 revolutions per minute; the fan and/or ventilator can preferably be operated at 500 to 800 revolutions per minute. The air heated by the detector device 5 and the components 15, 15' is transported by way of the exhaust air duct 16 to the air duct 17 and back to the cooling unit 12.

Figure 14:
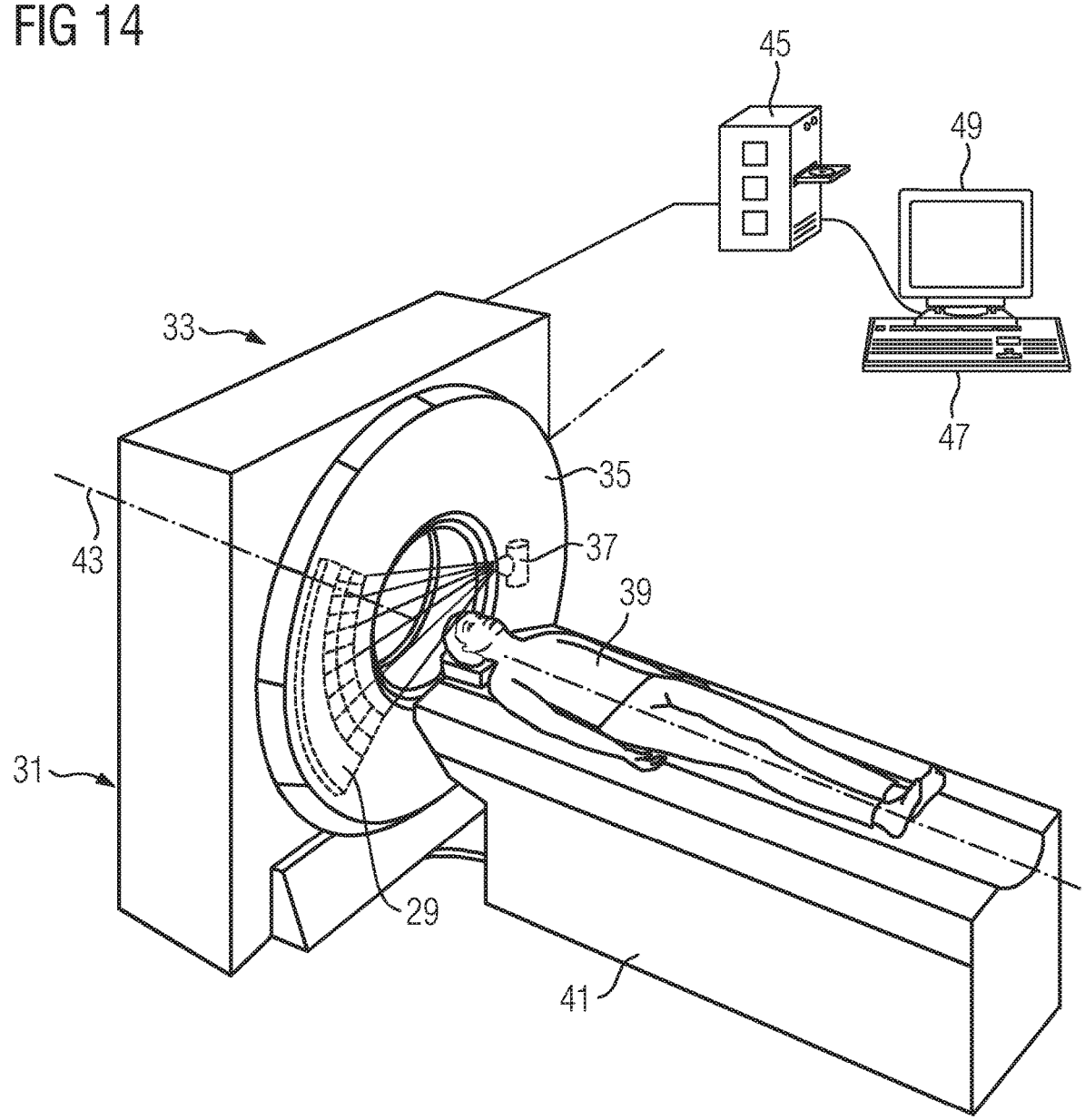
FIG. 14 A diagrammatic view of a computed tomography system according to an embodiment of the invention.

FIG. 14 shows an example embodiment of a computed tomography system 31 according to the invention with a detector device according to the invention. The computed tomography system 31 contains a gantry 33 with a rotor 35. The rotor 35 comprises the cooling circuit, an X-ray source 37 and a detector unit 29 comprising at least one detector device according to the invention. The patient 39 is accommodated on the patient table 41 and can be moved along the axis of rotation z 43 through the gantry 33. A computing unit 45 is used to control and calculate the cross-sectional images. An input device 47 and an output device 49 are connected to the computing unit 45.

Although the invention was illustrated in more detail by the preferred example embodiment, the invention is not restricted by the disclosed examples and other variations may be derived from this by a person skilled in the art without departing from the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A detector device, comprising:
    a cooling air pathway, formed by sidewalls, to cool an X-ray detector, a detector interior space surrounding the X-ray detector, the cooling air pathway running through at least one subregion of the detector interior space; and
    a pressure limitation unit including a limitation device, arranged along the cooling air pathway, the limitation device being designed to route a limited volume flow along the cooling air pathway at the X-ray detector, based on an incoming cooling air flow, wherein the limitation device includes a turbulence-producing body in the cooling air pathway.

2. The detector device of claim 1, wherein at least one of a height of the limitation device, a width of the limitation device, a depth of the limitation device, an inlet opening of the limitation device and an outlet opening of the limitation device is designed to limit a volume flow, based on an incoming cooling air flow.

3. The detector device of claim 2, further comprising:
    an air guide element, designed to route the limited volume flow along a subregion of the X-ray detector.

4. The detector device of claim 1, wherein the turbulence-producing body is a grid.

5. The detector device of claim 1, further comprising:
    an air guide element, between subregions of the detector interior space, designed to route the limited volume flow along at least one of the subregions of the X-ray detector.

6. The detector device of claim 1, further comprising:
    a heat sink, thermally coupled to the X-ray detector, the limited volume flow being configured to flow around the heat sink.

7. The detector device of claim 1, wherein the pressure limitation unit is arranged downstream relative to the detector interior space.

8. The detector device of claim 1, wherein the pressure limitation unit is arranged in the detector interior space.

9. The detector device of claim 8, wherein the pressure limitation unit is a heat sink.

10. The detector device of claim 1, wherein the pressure limitation unit is arranged upstream relative to the detector interior space and wherein the limitation device is designed, based on cooling air flowing into the pressure limitation unit, to route the limited volume flow from the pressure limitation unit along the cooling air pathway into the detector interior space.

11. The detector device of claim 10, wherein the limitation device includes a valve.

12. The detector device of claim 11, wherein the valve includes a switching point to automatically open the valve.

13. The detector device of claim 12, further comprising:
an air guide element, designed to route the limited volume flow along a subregion of the X-ray detector, wherein a partial flow rate routed through the valve is shielded from the subregion of the X-ray detector via the air guide element.

14. The detector device of claim 11, further comprising:
an air guide element, designed to route the limited volume flow along a subregion of the X-ray detector, wherein a partial flow rate routed through the valve is shielded from the subregion of the X-ray detector via the air guide element.

15. A medical device, comprising:
the detector device of claim 1; and
a cooling circuit including
a supply air duct, extending from an air duct to a cooling unit,
at least one cooling air duct, extending from the cooling unit to the detector device, and
an exhaust air duct, extending from the detector device to the air duct.

16. The medical device of claim 15, wherein the medical device is a computed tomography system.

17. The medical device of claim 16, wherein the air duct includes a rotor.

18. The medical device of claim 17, wherein at least one further cooling air duct is connected to a component.

19. The medical device of claim 16, wherein at least one further cooling air duct is connected to a component.

20. The medical device of claim 15, wherein at least one further cooling air duct is connected to a component.

21. The detector device of claim 1, wherein the pressure limitation unit is a heat sink.

22. The detector device of claim 1, wherein the limitation device is arranged upstream of the detector interior space in a direction of airflow along the cooling air pathway.

23. The detector device of claim 1, wherein the limitation device is an antechamber upstream of the detector interior space and is connected to the detector interior space via an outlet of the antechamber.

* * * * *